United States Patent [19]

Iovanni et al.

[11] Patent Number: 5,705,171
[45] Date of Patent: Jan. 6, 1998

[54] CLEAR COSMETIC STICK COMPRISING DIBENZYLIDENE ALDITOL

[75] Inventors: Carl F. Iovanni, Quincy; Tuan M. Vu, Brighton; Jayant N. Sane, Framingham, all of Mass.

[73] Assignee: The Gillette Company, Boston, Mass.

[21] Appl. No.: 695,839

[22] Filed: Jul. 10, 1996

Related U.S. Application Data

[63] Continuation of Ser. No. 397,450, Mar. 2, 1995, abandoned.

[51] Int. Cl.$^6$ ........................................ A16K 7/34
[52] U.S. Cl. ........................ 424/401; 424/65; 424/66
[58] Field of Search ........................ 424/65, 66, 68

[56] References Cited

U.S. PATENT DOCUMENTS

| | | | |
|---|---|---|---|
| H1473 | 8/1995 | Orofino et al. | 424/67 |
| 3,920,020 | 11/1975 | Kraskin | 128/284 |
| 3,981,986 | 9/1976 | Rubino | 424/47 |
| 4,017,599 | 4/1977 | Rubino | 424/47 |
| 4,150,024 | 4/1979 | Syldatk et al. | 260/239.3 R |
| 4,154,816 | 5/1979 | Roehl et al. | 424/68 |
| 4,346,079 | 8/1982 | Roehl | 424/65 |
| 4,383,988 | 5/1983 | Teng et al. | 424/68 |
| 4,502,975 | 3/1985 | Kobayashi et al. | 252/315.1 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,948,578 | 8/1990 | Burger et al. | 424/68 |
| 4,954,333 | 9/1990 | Ward | 424/66 |
| 5,106,999 | 4/1992 | Gardlik et al. | 549/364 |
| 5,168,378 | 12/1992 | Guthauser | 514/785 |
| 5,200,174 | 4/1993 | Gardlik et al. | 424/66 |
| 5,270,034 | 12/1993 | Cheng | 424/68 |
| 5,286,755 | 2/1994 | Kauffmann et al. | 514/944 |
| 5,346,694 | 9/1994 | Juneja | 424/66 |
| 5,368,848 | 11/1994 | Brazinsky et al. | 424/65 |
| 5,376,363 | 12/1994 | Benfatto et al. | 424/66 |
| 5,384,117 | 1/1995 | Vu et al. | 424/66 |
| 5,463,098 | 10/1995 | Giovanniello et al. | 556/27 |
| 5,516,511 | 5/1996 | Motley et al. | 424/65 |
| 5,520,907 | 5/1996 | Orofino et al. | 424/65 |
| 5,585,092 | 12/1996 | Trandai et al. | 424/65 |

FOREIGN PATENT DOCUMENTS

| | | |
|---|---|---|
| 0 260 030 B1 | 6/1988 | European Pat. Off. . |
| 0 404 532 A1 | 12/1990 | European Pat. Off. . |
| 0 451 002 A2 | 10/1991 | European Pat. Off. . |
| 0 599 775 A1 | 6/1994 | European Pat. Off. . |
| WO 91/15191 | 10/1991 | WIPO . |

OTHER PUBLICATIONS

The Merck Index (9th ed. 1976), p.778 (No. 5825).
Schwarzenbach, Complexometric Titrations (2nd English ed., 1969), pp. 145–155, 268–269.
Klepak, "Antiperspirants take a clear lead", *Manufacturing Chemist* (Nov. 1994), pp. 31–36.
Disorbene, Rouquette product brochure (1992).

*Primary Examiner*—Joseph L. Schofer
*Assistant Examiner*—Sharon Howard
*Attorney, Agent, or Firm*—Stephan P. Williams

[57] ABSTRACT

A clear gel cosmetic stick includes a liquid vehicle, a dibenzylidene alditol as a gelling agent, an antiperspirant salt dissolved in the liquid vehicle, and a chelating agent. The cosmetic stick comprises in percent by weight about 40% to about 95% of the liquid vehicle, from about 0.1% to about 5% of the dibenzylidene alditol, from about 0.5% to about 25% of the antiperspirant salt, and from about 0.05% to about 3% of the chelating agent. The cosmetic stick is preferably substantially free of alkaline gelling agent stabilizers such as NaOH and KOH.

37 Claims, No Drawings

CLEAR COSMETIC STICK COMPRISING DIBENZYLIDENE ALDITOL

This application is a continuation of Ser. No. 08/397,450 filed Mar. 2, 1995 now abandoned.

BACKGROUND OF THE INVENTION

The invention relates to clear gel cosmetic sticks which include a solubilized antiperspirant salt.

Gel antiperspirant sticks typically include a liquid vehicle, an antiperspirant salt, a gelling agent, and one or more emollients. Dibenzylidene alditols like dibenzylidene sorbitol (DBS), also known as dibenzylidene monosorbitol acetal (DBMSA), are one type of gelling agent that has been used in such sticks. Dibenzylidene alditols may degrade during manufacture and subsequent storage of the gel stick, in part because of the presence of the acidic antiperspirant salt in the stick. One product of the degradation, benzaldehyde, can provide an undesirable odor.

Various stabilizing agents have been incorporated into gel antiperspirant sticks containing dibenzylidene alditols in an effort to minimize dibenzylidene alditol degradation. Examples include sodium hydroxide, potassium hydroxide, sodium carbonate, zinc acetate, zinc oxide, zinc carbonate, potassium carbonate, diethanolamine, triethanolamine, disodium succinate, sodium benzoate, sodium octanoate, hexamethylenetetramine, urea, 2-amino-2-methyl-1-propanol, magnesium sulfate, calcium hydroxide, and N-(2-hydroxyethyl) acetamide. These and other stabilizing agents, although apparently effective to some degree in stabilizing the dibenzylidene alditol, may have other problems associated with them. Sodium hydroxide and potassium hydroxide, for example, may provide a composition with an undesirable odor.

Clear gel antiperspirant or deodorant sticks are more desirable than opaque sticks for cosmetic reasons.

SUMMARY OF THE INVENTION

The invention features a clear gel cosmetic stick that includes a liquid vehicle, a dibenzylidene alditol gelling agent, an antiperspirant salt, and a chelating agent. The cosmetic stick comprises in percent by weight about 40% to about 95% of the liquid vehicle, from about 0.1% to about 5% of the dibenzylidene alditol, from about 0.5% to about 25% of the antiperspirant salt, and from about 0.05% to about 3% of the chelating agent. The cosmetic stick is preferably substantially free of alkaline gelling agent stabilizers such as NaOH and KOH.

DETAILED DESCRIPTION OF THE INVENTION

A "clear" gel stick, as used herein, is a stick that is visually clear so that, like glass, it allows ready viewing of objects behind it. Preferred clear gel sticks have a turbidity measurement, expressed in Nephelometric Turbidity Units (NTU) of less than 150 NTU, more preferably less than 100 NTU, and most preferably less than 50 NTU, when measured with a Hellige #965 Direct-Reading Turbidimeter. Preferably the gel sticks are sufficiently clear to enable an observer to read without difficulty lettering of size 0.1 to 0.6 (more preferably greater than 0.4) on a visual acuity chart as given in the "Documenta Geigy Scientific Tables", published by Ciba-Geigy Ltd of Basle, Switzerland (1971 ed.).

By "substantially odor free" is meant that the gel stick (without any fragrance or fragrance masking agent) has an off-odor rating of 0 to 2, preferably 0 to 1, on a scale of 0 to 5 used by trained odor (or perfumery) experts, where 0 signifies no detectable off-odor and a rating of 4 to 5 is deemed unacceptable odor.

By "stable" is meant that samples of the product, when stored at 45° C. for three months, will not exhibit any noticeable benzaldehyde odor or other off-odor (i.e. retains an odor rating of 0 to 2) and will not exhibit any significant change in clarity or color (i.e. retains a clarity of better than 150 NTU and a color of 0 to 2 on the yellowness scale).

A "chelating agent", as used herein, is a compound in which atoms form more than one coordinate bond with metals in solution. Preferred chelating agents include tetrasodium- and trisodium-ethylenediaminetetraacetate ($Na_4EDTA$ and $Na_3EDTA$).

The preferred clear gel sticks include a liquid vehicle, a dibenzylidene alditol gelling agent, an antiperspirant salt, a chelating agent, a hydroxyalkyl cellulose co-gellant, one or more emollients, and a fragrance.

The liquid vehicle along with the gelling agents provide the matrix, or body, of the gel stick. Suitable liquid vehicles include one or more of the following: ethanol, n-propanol, isopropanol, n-butanol, isobutanol, t-butanol, 2-methoxyethanol, 2-ethoxyethanol, ethylene glycol, diethylene glycol, triethylene glycol, dipropylene glycol, tripropylene glycol, 1,2-propylene glycol, 1,3-propylene glycol, 1,4-butylene glycol, 1,2-butylene glycol, 1,3-butylene glycol, 2,3-butylene glycol, diethylene glycol monomethylether, diethylene glycol monoethylether, 2,4-dihydroxy-2-methylpentane, glycerin, sorbitol and the like, and mixtures thereof. Preferred liquid vehicles include polyhydric alcohols having from 3 to 6 carbon atoms and from 2 to 6 hydroxyl groups. More preferred are 1,2-propylene glycol (normally referred to simply as propylene glycol), dipropylene glycol, 1,3-butylene glycol, sorbitol and mixtures thereof. Most preferred as the liquid vehicle is propylene glycol, which may optionally include one or more of the aforementioned polyhydric alcohols. It is also most preferred that the liquid vehicle is substantially free (i.e., less than 2%) of monohydric alcohol such as ethanol. While the liquid vehicle may also optionally contain a co-solvent for the gelling agent, as described in the prior art, such is not preferred.

The gel stick generally includes between about 40% and about 95%, and preferably between about 50% and about 92%, of the liquid vehicle by weight. A stick including an insufficient quantity of the liquid vehicle may be unclear or may provide an inadequate support matrix for the remainder of the components. A stick including too much liquid vehicle may lack sufficient quantities of one or more of the other stick components.

The dibenzylidene alditol is the gelling agent. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(meta-chlorobenzylidene) sorbitol. The preferred gelling agent is dibenzylidene sorbitol (DBS).

The gel stick generally contains between about 0.1% and about 5%, preferably between about 0.5% and about 2%, more preferably less than about 1.5%, and most preferably between about 0.5% and about 1.3%, of the dibenzylidene alditol by weight. If the gel stick includes too much of the dibenzylidene alditol, it may lack sufficient clarity and/or may have an undesirable odor. If the gel stick includes too little of the dibenzylidene alditol it may lack sufficient hardness. A particularly advantageous feature of the present invention is the use of low levels (i.e. less than 1.5%) of the dibenzylidene alditol gelling agent, which results in sticks of exceptional clarity and odor-free characteristics.

Preferred gel sticks have a hardness of between about 40 and about 250, more preferably between about 60 and about 150, when measured on a TA-XT2 Texture Analyzer (Stable Micro System, Haste Hill, England). These hardness measurements correlate to the grams of force required for the standard arrowhead-type penetration needle to penetrate the stick a distance of 5 mm at 1 mm per second.

The preferred gel sticks will also include a hydroxyalkyl cellulose as an additional gelling agent (or co-gellant), which provides the preferred gel sticks with adequate hardness even when the sticks include only a low level of the dibenzylidene alditol. The combined use of the co-gellant with reduced amounts of the dibenzylidene alditol (i.e. amounts below 1.5%) enable the production of gel sticks of exceptional clarity and stability. The preferred hydroxyalkyl cellulose co-gellants include alkyl groups with between one and five carbon atoms. The preferred co-gellant is hydroxypropylcellulose (e.g. Klucel HFF, Aqualon). Preferred gel sticks include between about 0.08% and about 1%, more preferably between about 0.1% and about 0.5%, most preferably between about 0.2% and about 0.4%, of the hydroxyalkyl cellulose by weight.

Antiperspirant salts are metal salts that have significant antiperspirant activity when applied to the skin of a human, and include various inorganic and organic salts of aluminum, zirconium, and zinc. Many examples of these salts are known to those skilled in the art.

The preferred salts are any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$, wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$, wherein b is about 1 to 2, preferably about 1.2 to about 1.9. The preferred aluminum-zirconium salts have an Al:Zr ratio of about 1.7 to about 12.5, most preferably about 2 to about 8, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 8 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the gel sticks of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher.

To incorporate the antiperspirant salt in the gel stick composition, it is preferred that the salt is first solubilized in a portion of the liquid vehicle. Accordingly, it is preferred to utilize polyhydric alcohol solutions of antiperspirant salts, especially those which contain an additional alkaline glycinate, such as sodium, potassium, or zinc glycinate. Such solubilized antiperspirant salts are described in U.S. Ser. No. 08/397,451 filed on Mar. 2, 1995 pending entitled Method Of Making Polyhydric Alcohol Solutions Of Enhanced Efficacy Antiperspirant Actives, and in EP 599, 775, both of which are incorporated herein by reference. An example of such a solubilized salt, which is partially neutralized with zinc glycinate, is Westchlor A2Z 8106 (Westwood Chemical Corp.). The preparation of a preferred solubilized antiperspirant salt will be described below in conjunction with the examples of gel sticks.

The additional alkaline glycinate included in the antiperspirant salt raises the pH of the antiperspirant salt and, as a result, reduces the degradation of the dibenzylidene alditol in the gel stick. It is generally preferred to add sufficient alkaline glycinate to the antiperspirant salt so as to raise the pH of an approximately 10% aqueous solution of the antiperspirant salt to about 4.1 to 5.0, preferably about 4.4 to 5.0. (The aqueous solution may be an approximately 50:50 polyhydric alcohol:water solution.) Preferred gel sticks which include such a partially neutralized salt will have a pH greater than 4.4, preferably about 4.8 to about 5.5, and more preferably about 4.9 to about 5.3. The pH of the finished stick can be measured by dissolving one part stick in ninety-nine parts water.

The gel stick can be either an antiperspirant or a deodorant composition. Antiperspirant compositions generally include between 6% and about 25%, preferably between about 8% and about 22%, of the antiperspirant salt by weight. Deodorant compositions generally include between about 0.5% and about 6% of the antiperspirant salt by weight. It should be noted that reference throughout this application to weight percent of antiperspirant salt is intended to mean weight percent of the salt in accordance with conventional industry standards (i.e. including glycine and bound water).

Examples of chelating agents include EDTA (ethylenediaminetetraacetate) salts such as $Na_4EDTA$ and $Na_3EDTA$; hydroxyethylethylenediaminetriacetate (HEDTA); diethylenetriaminepentaacetate (DTPA); nitrilotriacetate (NTA); ethanoldiglycine disodium salt (EDG); diethanolglycine sodium salt (DEG); and 1,3-propylenediaminetetraacetic acid (PDTA). All of these are known and commercially available. The gel sticks generally include between about 0.05% and about 3%, preferably between about 0.1% and about 2%, of the chelating agent by weight. If too little chelating agent is included, the stick may have less clarity, an undesirable odor, and/or undesirable yellowness. If too much chelating agent is included, the clarity and/or other properties of the stick may be adversely affected.

The chelating agent may reduce the color (in particular the yellow color) of the stick that can result, for example, from the presence of residual iron (or other metal contaminants) that may be present in the stick from a variety of sources. The gel stick preferably measures 0–1 on the yellowness scale. Yellowness is measured by spectrophotometer at 408 nm with 0 corresponding to 0 ppm ferric chloride in water and 5 corresponding to 500 ppm ferric chloride in water.

The chelating agent may also act as a gelling agent stabilizer by increasing the pH of the stick, thus reducing or eliminating the need for other alkaline gelling agent stabilizers such as NaOH and KOH. The gel sticks preferably are substantially free of NaOH and KOH and, as a result, do not have the odor that can result from the interaction of these materials with the vehicle, particularly with propylene glycol. The elimination of other alkaline gelling agent stabilizers, particularly NaOH and KOH, is a key feature of the present invention and is believed to substantially contribute to the odor-free characteristics of the gel sticks of the present invention.

The preferred gel sticks retain one or more of the above-described properties, more preferably all of the above-described properties, even after storage at 45° C. for three months.

The emollients provide the gel stick with desirable application properties (smoothness, reduced tack, etc.). Examples of emollients include fatty acid esters such as isopropyl myristate and isopropyl palmitate; diesters of adipic, phthalic, and sebacic acids such as di-n-butyl phthalate, diisopropyl sebacate, diethyl sebacate, and diisopropyl adipate; propylene glycol diesters of short chain fatty acids; nonvolatile silicone oils such as dimethyl siloxane and dimethicone copolyol; volatile silicones such as Dow Corning 344 and Dow Corning 345 (available from Dow Corning), Silicone 7207 and Silicate 7158 (available from Union Carbide), and SF 1202 (available from General Electric); $C_{12}$–$C_{15}$ alcohol benzoates such as Finsolv (available from Finetex, Inc.); fatty alcohols such as cetyl alcohol and stearyl alcohol; alkyl ether derivatives of polyethylene glycols, polypropylene glycols and polypropylene polyethylene glycol copolymers such as PPG-5-Buteth-7, PPG-5-Ceteth-20, PPG-3-1sosteareth-9 and Glycereth-7-Diisononanoate. Many other examples of emollients are known in the art. The gel sticks should include a sufficient quantity of emollient to provide the stick with the desired application properties without interfering with the clarity of the product. The preferred emollients should be soluble in the liquid vehicle and form a clear solution therein. The gel sticks preferably include less than about 10%, more preferably less than about 3%, and most preferably between about 0.25% and 1.25%, of emollients by weight.

The fragrances used in the gel stick can be any conventional fragrance that provides the stick with a desired scent. The quantity of fragrance included should be the quantity needed to provide the desired scent. The gel stick generally includes less than about 2.5%, preferably less than about 1.5%, of the fragrance by weight.

The gel sticks can contain other optional conventional ingredients such as humectants, hardeners such as waxes, fillers, colorants, preservatives, bacteriocides, UV absorbers, and the like.

The following specific examples further illustrate the invention:

EXAMPLE 1

Antiperspirant Salt

A 50% sodium glycinate solution was prepared by mixing 171 lbs. (77.6 kg) 50% NaOH with 67.8 lbs. (30.8 kg) water, then adding 160.3 lbs (72.8 kg) of glycine (1:1 mole ratio of glycine to NaOH), the temperature rising from 25° to 30° C., then from 30° to 35° C., after the first and second additions respectively. To 103.3 lbs. (46.9 kg) of propylene glycol was added 7.8 lbs. (3.5 kg) of 50% sodium glycinate and the solution mixed for ten minutes. To this solution was added 33.9 lbs. (15.4 kg) of zirconium hydroxychloride glycinate (50% aqueous ZHC-gly solution with a Zr:gly ratio of about 1:1). After mixing this solution for about ten minutes, 255 lbs. (115. Bkg) of 10% ACH' solution (prepared by heating 10% ACH at about 80° C. for about 16 to 17 hours) was added and mixed for about ten minutes. This solution was preheated to about 70° to 75° C. and fed continuously to a type JHE flash evaporator (APV Crepaco Inc., Tonawanda, N.Y.; evaporator modified by mounting to the top of the flash chamber a 3 foot rectification tower filled with about 2.5 feet of 0.5 inch ceramic Berl saddles) maintained at about 60 mm Hg (absolute pressure) from which was withdrawn at about 1 gal/hr a clear solution comprising 65% propylene glycol, 30% enhanced efficacy aluminum-zirconium tetrachlorhydrate-glycine (more than 80% of aluminum in peaks 3 and 4 with peak 4 to peak 3 area ratio greater than 1 and Gly:Zr ratio about 1.6:1 ), and 5% water. The pH of a sample of this solution diluted with an equal portion of distilled water was about 4.7. This antiperspirant salt solution was incorporated into the following examples.

EXAMPLES 2 and 3

| Ingredient | Ex. 2 Wt. % | Ex. 3 Wt. % |
|---|---|---|
| Propylene glycol | 85.60 | 84.80 |
| Al/Zr tetrachlorohydrate-gly | 11.00* | 11.00* |
| Dibenzylidene sorbitol | 1.00 | 1.30 |
| Na$_4$EDTA | 0.10 | 0.10 |
| Dimethicone copolyol (ABIL B 8851) | 0.25 | 0.25 |
| Hydroxypropyl cellulose | 0.30 | 0.30 |
| Fragrance | 1.25 | 1.25 |
| Diisopropyl sebacate | — | 1.00 |
| Glycereth-7-diisononanoate | 0.50 | — |

*Weight % of salt in final composition. Salt is added in solubilized form as prepared in Example 1.

Examples 2 and 3 were prepared according to the following procedure.

Phase A:

About 65% of the total propylene glycol mass (excluding that which is part of the antiperspirant salt solution) is added to an appropriately sized vessel. Hydroxypropyl cellulose is added and stirred well to dissolve. After heating this solution to 110°–115° C., the dibenzylidine sorbitol is added with stirring until completely dissolved. This Phase A solution is then cooled to about 100° C.

Phase B:

About 35% of the total propylene glycol mass (excluding that which is part of the antiperspirant salt solution) is added to an appropriately sized vessel, stirred and heated to about 60°–70° C. The Na$_4$EDTA is added and mixed well. The Al/Zr tetrachlorohydrate-gly solution (as prepared in Example 1) is added and the solution mixed well until it becomes clear and homogenous. The emollients (i.e. diisopropyl sebacate or glycereth-7-diisononanoate and the dimethicone copolyol) are then added and the Phase B solution is mixed well until clear.

Combined Phase:

Phase B is added to phase A with mixing and cooled to about 80° C. The fragrance is added and allowed to mix well. The product is poured into suitable stick containers and cooled to solidify.

EXAMPLES 4 and 5

| Ingredient | Ex. 4 Wt. % | Ex. 5 Wt. % |
| --- | --- | --- |
| Propylene glycol | 86.00 | 83.30 |
| Hydroxypropyl cellulose | 0.30 | — |
| Dibenzylidene sorbitol | 0.50 | 0.50 |
| Al/Zr tetrachlorohydrate-gly | 11.00* | 11.00* |
| Na$_4$EDTA | 0.20 | 0.20 |
| Glycereth-7-diisononanoate | 0.50 | 0.50 |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

Examples 4 and 5 were prepared by procedures analogous to the procedure used to prepare examples 2 and 3.

EXAMPLE 6

| Ingredient | Wt. % |
| --- | --- |
| Propylene glycol | 84.95 |
| Hydroxypropyl cellulose | 0.30 |
| Dibenzylidene sorbitol | 1.00 |
| Al/Zr tetrachlorohydrate-gly | 11.00* |
| Glycereth-7-diisononanoate | 0.50 |
| Dimethicone copolyol | 0.25 |
| NaOH | 0.55 |
| Na$_4$EDTA | 0.20 |
| Fragrance | 1.25 |

*Weight % of salt in final composition. Salt is added in solubilized form without added glycinate.

Example 6 was prepared by a procedure analogous to the procedure used to prepare examples 2 and 3.

EXAMPLE 7

Deodorant

| Ingredient | Wt. % |
| --- | --- |
| Propylene glycol | 93.75 |
| Al/Zr tetrachlorohydrate-gly | 2.00* |
| Na$_4$EDTA | 0.20 |
| Dibenzylidene sorbitol | 1.30 |
| Hydroxypropyl cellulose | 0.50 |
| Oleth-10 | 0.75 |
| PPG-10 butanediol | 0.75 |
| PPG-3 myristyl ether | 0.75 |

*Weight % of salt in final composition. Salt is added in solubilized form as prepared in Example 1.

Example 7 was prepared by a procedure analogous to the procedure used to prepare examples 2 and 3.

What is claimed is:

1. A clear gel cosmetic stick comprising a liquid vehicle, a gelling agent comprising dibenzylidene alditol, an antiperspirant salt dissolved in said liquid vehicle, and a chelating agent.

2. The cosmetic stick of claim 1 wherein said liquid vehicle comprises a polyhydric alcohol having from 3 to 6 carbon atoms and from 2 to 6 hydroxyl groups.

3. The cosmetic stick of claim 2 wherein said antiperspirant salt comprises aluminum chlorohydrate or aluminum zirconium chlorohydrate.

4. The cosmetic stick of claim 3 wherein said antiperspirant salt is partially neutralized with alkaline glycinate.

5. The cosmetic stick of claim 3 or 4 wherein said dibenzylidene alditol comprises dibenzylidene sorbitol.

6. The cosmetic stick of claim 5 wherein said chelating agent is selected from the group consisting of tetrasodium ethylenediaminetetraacetate, trisodium ethylenediaminetetraacetate, hydroxyethylethylenediaminetriacetate, diethylenetriaminepentaacetate, nitrilotriacetate, ethanoldiglycine disodium salt, ethylenediaminetetraacetate or trisodium etheylenediaminetetraacetate, diethanolglycine sodium salt, and 1,3-propylenediaminetetraacetic acid.

7. The cosmetic stick of claim 5 wherein said chelating agent is tetrasodium ethylenediaminetetraacetate or trisodium ethylenediaminetetraacetate.

8. The cosmetic stick of claim 7 wherein said polyhydric alcohol comprises propylene glycol.

9. The cosmetic stick of claim 1 wherein said chelating agent is selected from the group consisting of tetrasodium ethylenediaminetetraacetate, trisodium ethylenediaminetetraacetate, hydroxyethylethylenediaminetriacetate, diethylenetriaminepentaacetate, nitrilotriacetate, ethanoldiglycine disodium salt, diethanolglycine sodium salt, and 1,3-propylenediaminetetraacetic acid.

10. The cosmetic stick of claim 1 wherein said chelating agent is tetrasodium ethylenediaminetetraacetate or trisodium ethylenediaminetetraacetate.

11. The cosmetic stick of claim 1 which comprises in percent by weight about 40% to about 95% of said liquid vehicle, from about 0.1% to about 5% of said dibenzylidene alditol, from about 0.5% to about 25% of said antiperspirant salt, and from about 0.05% to about 3% of said chelating agent.

12. The cosmetic stick of claim 1 which comprises in percent by weight about 50% to about 92% of said liquid vehicle, from about 0.5% to about 1.5% of said dibenzylidene alditol, from about 1% to about 22% of said antiperspirant salt, and from about 0.1% to about 2% of said chelating agent.

13. The cosmetic stick of claim 12 which further comprises a hydroxyalkyl cellulose.

14. The cosmetic stick of claim 13 which comprises from about 0.08% to about 1% of hydroxypropyl cellulose by weight.

15. The cosmetic stick of claim 12 wherein said liquid vehicle comprises a polyhydric alcohol having from 3 to 6 carbon atoms and from 2 to 6 hydroxyl groups.

16. The cosmetic stick of claim 15 wherein said antiperspirant salt comprises aluminum chlorohydrate or aluminum zirconium chlorohydrate.

17. The cosmetic stick of claim 16 wherein said antiperspirant salt is partially neutralized with alkaline glycinate.

18. The cosmetic stick of claim 16 or 17 wherein said dibenzylidene alditol comprises dibenzylidene sorbitol.

19. The cosmetic stick of claim 18 wherein said chelating agent is tetrasodium ethylenediaminetetraacetate or trisodium ethylenediaminetatraacetate.

20. The cosmetic stick of claim 19 which comprises from about 0.08% to about 1% of hydroxypropyl cellulose by weight.

21. The cosmetic stick of claim 20 wherein said polyhydric alcohol comprises propylene glycol.

22. The cosmetic stick of claim 17 which has a pH of about 4.8 to about 5.5.

23. The cosmetic stick of claim 22 which is substantially free of sodium hydroxide and potassium hydroxide.

24. The cosmetic stick of claim 23 wherein said chelating agent is tetrasodium ethylenediaminetetraacetate or trisodium ethylenediaminetetraacetate.

25. The cosmetic stick of claim 24 which further comprises from about 0.08% to about 1% of hydroxypropyl cellulose by weight.

26. The cosmetic stick of claim 25 which further comprises from about 0.1% to about 2% of an emollient by weight.

27. The cosmetic stick of claim 26 wherein said cosmetic stick is an antiperspirant that comprises from about 8% to about 22% of said antiperspirant salt by weight.

28. The cosmetic stick of claim 26 wherein said cosmetic stick is a deodorant that comprises from about 1% to about 6% of said antiperspirant salt by weight.

29. The cosmetic stick of claim 1, 24 or 26 wherein said cosmetic stick has a turbidity of less than about 100 NTU.

30. The cosmetic stick of claim 1, 24 or 26 wherein said cosmetic stick is sufficiently clear to enable an observer to read without difficulty lettering of size 0.1 to 0.6 on a visual acuity chart.

31. The cosmetic stick of claim 29 which has a hardness of about 60 to about 150.

32. The cosmetic stick of claim 31 which has a color of 0 to 1 on the yellow scale.

33. The cosmetic stick of claim 32 which is substantially odor free.

34. The cosmetic stick of claim 33 which is stable with respect to clarity, color and odor when stored at 45° C. for 3 months.

35. A clear gel cosmetic stick comprising in percent by weight about 50% to about 92% of a liquid vehicle comprising a polyhydric alcohol having from 3 to 6 carbon atoms and from 2 to 6 hydroxyl groups, about 0.5% to about 1.5% of dibenzylidene sorbitol, about 1% to about 22% of an antiperspirant salt selected from aluminum chlorohydrate and aluminum zirconium chlorohydrate, said antiperspirant salt being solubilized in said vehicle and partially neutralized with alkaline glycinate, about 0.08% to about 1% of hydroxyalkyl cellulose, and about 0.1% to about 2% of a chelating agent selected from tetrasodium ethylenediaminetetraacetate and trisodium ethylenediaminetetraacetate, wherein said stick has a pH of about 4.8 to about 5.5, a turbidity of less than about 100 NTU, and a hardness of about 60 to about 150.

36. A clear gel antiperspirant stick comprising in percent by weight about 50% to about 92% of a liquid vehicle comprising a polyhydric alcohol having from 3 to 6 carbon atoms and from 2 to 6 hydroxyl groups, said liquid vehicle being substantially free of monohydric alcohol, about 0.5% to about 1.5% of dibenzylidene sorbitol, about 8% to about 22% of an antiperspirant salt, said antiperspirant salt being solubilized in said vehicle, about 0.05% to about 3% of a chelating agent, and about 0.08% to about 1% of hydroxyalkyl cellulose, wherein said stick has a pH greater than 4.4, a turbidity of less than about 100 NTU, and is substantially free of sodium hydroxide and potassium hydroxide.

37. The antiperspirant stick of claim 36 comprising about 0.1% to about 2% of a chelating agent selected from tetrasodium ethylenediaminetetraacetate and trisodium ethylenediaminetetraacetate.

* * * * *